United States Patent [19]

Franchimont et al.

[11] Patent Number: 5,670,538
[45] Date of Patent: Sep. 23, 1997

[54] USE OF PRODELPHINIDINS FOR OBTAINING MEDICAMENTS INTENDED FOR THE TREATMENT OF ARTHROSIS

[75] Inventors: Paul Franchimont, deceased, late of Modave, Belgium, by Marie-Claire Céline Berthe Roelandts, administrator; Corine Bassleer, Liege, Belgium; Luc Angenot, Flemalle, Belgium; Monique Tits, Vottem, Belgium

[73] Assignee: Laboratoires Dolisos, Paris, France

[21] Appl. No.: 464,782

[22] PCT Filed: Dec. 28, 1993

[86] PCT No.: PCT/FR93/01312

§ 371 Date: Nov. 20, 1995

§ 102(e) Date: Nov. 20, 1995

[87] PCT Pub. No.: WO94/14432

PCT Pub. Date: Jul. 7, 1994

[30] Foreign Application Priority Data

Dec. 28, 1992 [FR] France ................... 92 15801

[51] Int. Cl.$^6$ ................... A61K 31/35
[52] U.S. Cl. ................... 514/456; 514/457
[58] Field of Search ................... 514/456, 457

[56] References Cited

U.S. PATENT DOCUMENTS 4,268,517 5/1981 Niebes et al. ................... 424/283
4,698,360 10/1987 Masquelier ................... 514/456

FOREIGN PATENT DOCUMENTS

WO92/14457 9/1992 WIPO.

OTHER PUBLICATIONS

"Anti–Inflammatory Prodelphinidins from Black Currant (Ribes nigrum) Leaves", *Planta Med.*, vol. 57, Supl. 1991, p. A131, by M. Tits et al.

"Evidence by in vivo and in vitro studies that binding of pycnogenols to elastin affects its rate of degradation by elastases", *Biochemical Pharmacology*, vol. 33, No. 24, 1984, pp. 3933–3939, by J.M. Tixier et al.

*Primary Examiner*—Theodore J. Criares
*Attorney, Agent, or Firm*—Young & Thompson

[57] ABSTRACT

A subject of the invention is the use of prodelphinidins for obtaining medicaments intended for the treatment of articular pathologies associated with the destruction of the cartilage, and more particularly of arthrosis.

7 Claims, No Drawings

USE OF PRODELPHINIDINS FOR OBTAINING MEDICAMENTS INTENDED FOR THE TREATMENT OF ARTHROSIS

This application is filed under 35 U.S.C. 371 of PCT/FR93/01312 filed Dec. 28, 1993 which claims priority of application FR 92/15801 filed in France Dec. 28, 1992.

A subject of the present invention is the use of prodelphinidins, and more particularly those obtained from the Ribes species, in particular *Ribes nigrum*, for obtaining medicaments intended for the treatment of arthrosis.

Under normal conditions, the articular cartilage undergoes slow reshaping via a chondroresorption mechanism perfectly compensated for by a chondrorepair process (or chondroformation) which maintains the articular cartilage in dynamic equilibrium (Franchimont et al., 1991).

The chondroresorption is provided by the chondrocyte itself which produces prostaglandins amongst which are PGE2, proteolytic enzymes (collagenase, stromelysine, serine proteases . . . ) and oxygen free radicals which attack the cartilage matrix, disrupt it and destroy it.

At the same time as this chondroresorption, a homeostatic chondroformation takes place which repairs the altered and/or resorbed material; macromolecules are produced which form the structure of the basic substance: collagens of type II and type IX, proteoglycans, junction proteins, etc . . . . The clonal proliferation of chondrocytes can be assisted when chondroformation must be significant. This chondroformation phase is a process dependent on several factors amongst which are the concentration of macromolecules of the areas close to the chondrocyte and the hormonal balance, in particular the secretion of growth hormone, IGF I and II, calcitonin, androgens . . .

Various pathogenic factors can arise which accelerate the degradation of the cartilage by acceleration of the chondroresorption process disturbing the equilibrium between chondroresorption and chondrorepair in favour of the former. These are, amongst others, articular functional and weight overloads, deposits of microcrystals and nutritional disorders of the articular structures. These pathogenic factors act by stimulating the production of cytokines (I L1 beta, TNF alpha, IL6 . . . ) by the chondrocytes themselves, by other cells of neighbouring structures such as the A synoviocytes of the articular synovial membrane. The imbalance will be all the more marked if hormonal disturbances exist (as is the case after 50, the age at which arthrosis can develop) making chondrorepair less effective.

This biochemical imbalance leads to a weakening of the articular cartilage which first of all cracks on the surface then more deeply exposing the sub-chondral bone. Arthrosis is the clinical expression of this loss of cartilage function, which is itself a consequence of the biochemical imbalance between chondroresorption and chondrorepair.

The treatment of arthrosis using medicaments is poor: non-steroid anti-inflammatories combat pain and improve movement; they do not stop the development of the disease, in particular the destruction of cartilage, and they do not enable cartilage to be repaired.

In particular, the use of pyknogenols originating from plant extracts such as *Ribes nigrum*, for the preparation of medicaments with an anti-inflammatory activity, is the subject of the International Application WO 92/14457 of the 14th Feb. 1992.

Furthermore, the use of proanthocyanidins for the prevention or the treatment of pathologies due to the biological effects of free radicals, in particular inflammations, is the subject of the U.S. Pat. No. 4,698,360 filed on 9th Apr. 1985.

A specific aim of the present invention is to provide medicaments which, by their properties for reducing chondroresorption and stimulating chondrorepair, allow the effective treatment of arthrosis or any other pathology directly or indirectly associated with destruction of cartilage and the absence of repair of the latter by the biological mechanisms of the organism.

A subject of the present invention is the use of prodelphinidins of formula (I):

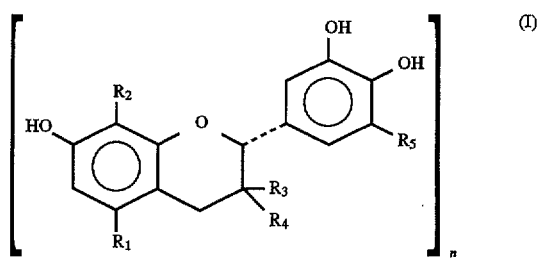

in which:

$R_1$ and $R_2$ independently represent H or OH, $R_3$ and $R_4$ are different and represent H or OH, $R_5$ represents H (catechin/epicatechin) or OH (gallocatechin/epigallocatechin), and, n is an integer from 2 to 40, under the condition that at least one of the 2 to 40 units described above corresponds to a gallocatechin ($R_3$=H, $R_4$=OH), or to an epigallocatechin ($R_3$=OH, $R_4$=H), for which $R_5$ represents OH, for obtaining medicaments intended for the treatment of articular pathologies associated with destruction of the cartilage, and more particularly of arthrosis.

A more particular subject of the invention is the above-mentioned use of prodelphinidins chosen from those corresponding to the following formula (II):

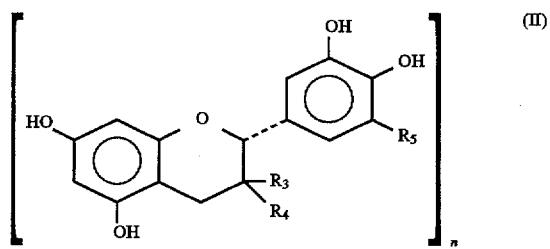

in which $R_3$, $R_4$ and $R_5$ are as defined above within the scope of formula (I).

By their properties for the stimulation of the production of proteoglycans and collagens (in particular of type II) in cartilage, the prodelphinidins according to the invention are capable of restoring the chondroformation process.

These prodelphinidins have in addition the advantage of reducing chondroresorption, in particular by their effects of reduction of the production of prostaglandins (in particular of type E2) and of reduction of the production of free radicals in the organism.

The medicaments according to the invention are more particularly intended for administration by oral, parenteral or topical route.

Preferably, the prodelphinidins contained in these medicaments are those from plants, and more particularly from the Ribes species, in particular *Ribes nigrum*.

The plants from which said prodelphinidins are isolated are obtained by standard methods in the field, or by in vitro production techniques.

According to an embodiment of the invention, the above-mentioned medicaments contain extracts of the Ribes species, and more particularly of *Ribes nigrum*, these extracts themselves containing prodelphinidins.

These Ribes extracts, in particular of *Ribes nigrum*, can advantageously be obtained according to the following processes.

In a first advantageous process for preparing a Ribes extract, a batch of leaves is pulverized and is extracted using slow percolation by means of ethanol at 70°. After obtaining the last percolate, the powder is squeezed out and all the extractive solutions are collected together. The ethanol is eliminated by distillation using a rotary evaporator, under reduced pressure, at a temperature of less than 50° C. The remaining aqueous solution is filtered in order to eliminate most of the chlorophyll. Then fractionation is carried out successively using solvents of increasing polarity, such as a) diethyl ether in order to eliminate the remaining chlorophyll and various liposoluble substances;

b) ethyl acetate;

c) n-butanol.

In another advantageous extraction process a batch of Ribes dried leaf powder is extracted using slow percolation, by means of an acetone-water mixture. After obtaining the last percolate, the powder is squeezed out using a press and all the liquids are collected together. The total extract can be vigorously agitated with NaCl, added until two phases are obtained; an upper acetonic phase and a lower aqueous phase. The acetonic phase is evaporated under reduced pressure at 30° C. and the aqueous residue has added to it an equal volume of water, followed by filtering then re-extraction; either with ethyl acetate, or with butanol. The extracts are then evaporated to dryness.

In this way extracts are obtained containing at least 2% by weight of prodelphinidins of formula (I) or (II).

According to another particularly advantageous embodiment of the invention, the prodelphinidins contained in the medicaments mentioned above are isolated and purified from plant extracts which can contain said prodelphinidins, and more particularly from plants belonging to the Ribes species, in particular *Ribes nigrum*.

The isolation and purification of prodelphinidins from the plants mentioned above, and more particularly from *Ribes nigrum*, is advantageously carried out by different chromatographic techniques on gel, or also by ultra-filtration techniques known to a man skilled in the art, from extracts obtained according to the processes described above.

Among the chromatographic techniques, there will be mentioned in particular the use of the Fractogel TSK column (MERCK, USA) eluting with water, then with a water/methanol mixture with an increasing percentage of methanol; the Sephadex LH 20 column (PHARMACIA, SWEDEN) eluting with alcohol, then alcohol with water added to it; or also on a Lobar Lichroprep RP8 column (MERCK, U.S.A.), elution being carried out with a water/acetone mixture.

These different techniques can be combined together in order to obtain a higher degree of purity.

The medicaments which are particularly preferred within the scope of the present invention are characterized in that they contain prodelphinidins chosen from at least one of the following molecules (Ia), (Ib) and (Ic):

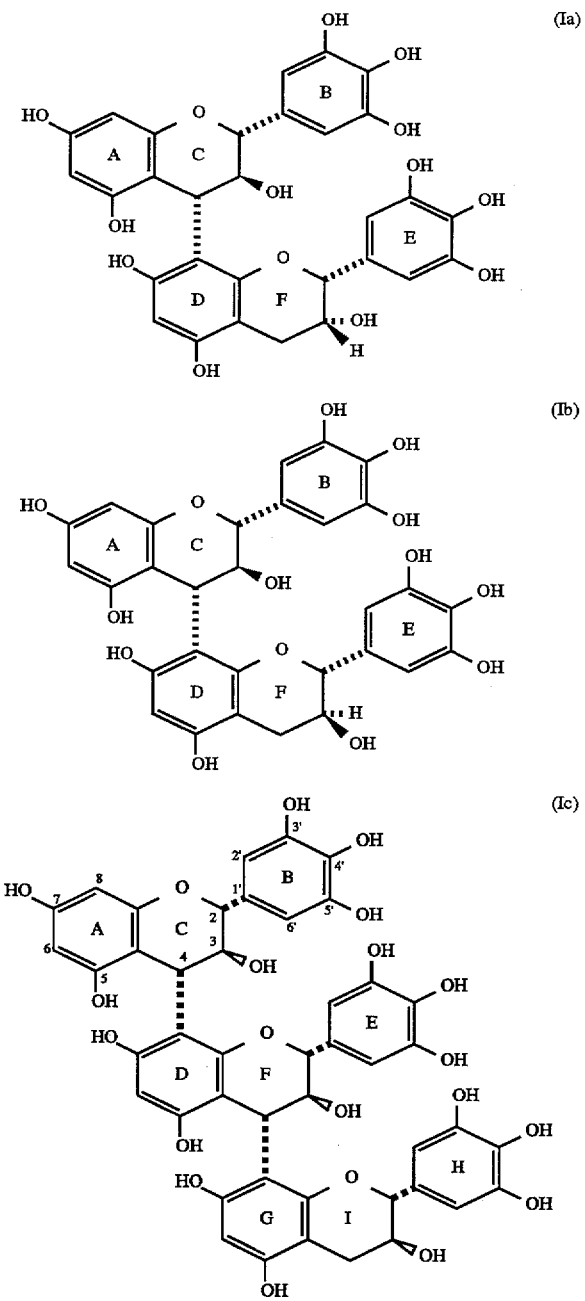

The invention will be further illustrated in the detailed description which follows of the effect of compositions based on prodelphinidins according to the invention, on chondrorepair and chondroresorption.

The model used for testing the proanthocyanidols, namely the tridimensional culture of human chondrocytes allows chondrorepair to be quantified by the production of matrix substances: type II collagen, proteoglycans, and chondroresorption by the reduction in the levels of prostaglandin E2 and of $OH°$ and $O°_2$ type free radicals produced.

I) EQUIPMENT AND METHODS (Franchimont et al., 1989)

1. Tridimensional culture of human chondrocytes

The technique used has been described in detail (Bassleer et al., 1986).

Briefly, human articular chondrocytes are cultivated in DMEM (Dulbecco's Modification of Eagle's Medium—

ICN—Gand, Belgium) with either Ultroser G 1% (GIBCO, Gand, Belgium) or 10% of foetal calf serum (ICN—Gand—Belgium), and 50 µg of ascorbic acid/ml added to it. The cartilage originates from the apparently normal zone of heads of human femur suffering from arthrosis, immediately after an operation carried out to insert a total hip prosthesis; it can also originate from the head of a healthy femur, but which has undergone a traumatism and has had to be replaced. This cartilage is then digested by clostridial collagenase 1 mg/ml (Boehringer-Mannheim, Germany) in a buffer (NaCl 120 mM, $CaCl_2$ 1 mM, KCl 5 mM, $KH_2PO_4$ 1 mM, $NaHCO_3$ 25 mM, glucose 2 mM and Hepes 30 mM, pH 7.4) for 24 hours. After 6 successive washings and centrifugations, the chondrocytes, isolated from their matrix, are cultured in flasks ($10^6$ cells/2 ml of culture medium) placed on a gyrator (10 rpm). The cultures are kept at 37° C. in an atmosphere of air 95%-$CO_2$ 5% (Bassleer et al., 1986). Cultivated under these conditions, after 4 to 5 days the chondrocytes form a tridimensional cluster in each flask. These clusters, which at first have a flocculent appearance, then tend to condense during the culture. After two weeks, their diameter is, in general, from 1 to 2 mm.

The fresh weight of the clusters increases with the duration of the culture, above all during the few first days.

2. Radioimmunoassay of cartilaginous proteoglycans (PG)

The PGs are measured with a radioimmunoassay (RIA) which is specific and sensitive to human cartilaginous PGs (Gysen et al. 1984). The PGs were extracted from human cartilage, according to the methods described by Roughley et al., (1981) and by Bayliss and Venn (1980). The antiserum against the cartilaginous PGs was obtained from the rabbit according to the technique of Vaitukaitis et al. (1971). The radioimmunoassay is carried out in a 0.4 ml volume consisting of 0.1 ml of tracer solution (15000 to 20000 cpm $^{125}$I-PG, labelled by the chloramine T method (Greenwood, 1973). 0.1 ml of anti-PG antiserum diluted to 1/5000 in phosphate-buffered saline (PBS-50 mM $PO_4$, 150 mM NaCl), containing BSA (5 g/l bovine serum albumin and 6.7 mM sodium azide) (incubation buffer) and 0.2 ml of several dilutions of the culture medium or of the cluster extract or also of the antigen (0.5–500 ng/tube).

After four days at 4° C., the free PGs* (radioactive PGs) are separated from the PG*-antibody complexes by double precipitation (Franchimont et al., 1983).

The sensitivity of the assay is 0.6 ng/tube. The accuracy of measurement is of the order of 4%. The coefficients of the intra- and inter assay variation are less than 10% and 20% respectively.

The antibodies are directed against the antigenic determinants of the central protein of PG. There is a complete crossed reaction with human PGs of cartilage from the ribs, vertebral disks and trachea, even with PGs extracted from veins or arteries. There is no cross reaction with glycosaminoglycans or with PGs extracted from foetal tissues or the small PGs from bone. Moreover, the assay is specific to the species, as PGs extracted from the cartilage of embryonic dogs, rats, chickens or calves do not react in the assay. Type II collagen, fibronectin, chondroitin sulphate and hyaluronic acid do not interfere in the assay.

The PGs are measured directly in the culture medium. As for the chondrocyte clusters, they are washed 3 times in a phosphate-buffered saline (PBS-50 mM $PO_4$, 150 mM NaCl pH 7.4) containing protease inhibitors (Oegema et al., 1975:100 mM 6-aminohexanoic acid, 10 mM EDTA, 50 mM benzamidine hydrochloride, $5.10^{-8}$M trypsin inhibitor, 6.7 mM sodium azide and 200 U/ml superoxide dismutase).

The clusters are homogenized in the same buffer by dissociation with ultrasonics (10 seconds, at 4° C., power 200 watts/$cm^2$). This extraction allows 70 to 80% of the PGs extracted with HCl-guanidine to be obtained.

3. Radioimmunoassay of type II collagen (coll. II)

The method for the radioimmunoassay of coll. II has been described in detail (Henrotin et al., 1990). The coll. II is extracted from human articular cartilage according to the technique described by Herbage et al. (1977). The antiserum against coll. II was obtained from rabbits according to the technique of Vaitukaitis et al. (1971).

The assay is carried out by sequential saturation. In the first instance, the radioimmunoassay is carried out in a 0.3 ml volume consisting of 0.2 ml of incubation buffer (PBS-50 mM $PO_4$, 300 mM NaCl, 5 g/l BSA (W/V), 6.7 mM sodium azide, pH 7.4) containing the reference coll. II (0.5 to 500 ng) or the sample to be assayed and 0.1 ml of anti-coll. II antiserum from guinea pigs diluted to 1/5000 (24 hours at 4° C.). In the second instance, 0.1 ml of $^{125}$I-coll. II tracer labelled according to the iodogenic technique (Salacynski et al., 1979 and diluted so as to obtain 20,000 cpm/0.1 ml) is added. After 24 hours at 4° C., the collagen-antibody complexes are separated from the free radioactive coll. II by the double antibody system (Franchimont et al. 1983). Sequential saturation gives a sensitivity of 3 ng/tube. The accuracy of the method is 10%. The coefficients of the intra- and inter assay variation are 10% and 20% respectively.

The assay is specific to human articular type II collagen. There is no cross reaction with other cartilage constituents: human PGs, fibronectin, laminin and hyaluronic acid do not interfere in the assay.

No cross reaction is obtained with bovine collagen of type I, III or IV.

The culture media are stored at −20° C. in the presence of enzymatic inhibitors (Oegema et al., 1975). These media are assayed by the radio immunological method without any treatment beforehand. The chondrocyte clusters are washed and dissociated with ultrasonics according to the method described for the assay of the PGs. After centrifugation (1500 rpm, 10 minutes), the residue is extracted using 500 mM acetic acid under agitation for 24 hours at 4° C. The supernatant of the homogenate and the extract of the residue are mixed together and assayed after equilibration at pH 7.4 using 4M NaOH.

The recovery of coll. II is 88±8% (x±1 s.d.).

4. Radioimmunoassay of prostaglandins E2 (PGE2)

The radioimmunoassay of PGE2s is carried out according to the method described by Serteyn et al., 1988. The PGE2 is obtained from Sigma (Aldrich-Chemie, Steinheim, Germany) and the $^3$H-PGE2 from NEN (Du Pont de Nemours, Brussels, Belgium). 0.1 ml of incubation buffer (10 mM Tris-HCl 150 ml NaCl, 0.5% sodium azide (W/V), 1% gelatine (W/V), pH 7.4), 0.1 ml of $^3$H-PGE2 (diluted so as to obtain 10,000 cpm/0.1 ml) and 0.1 ml of antiserum (1/4000) are added successively to 0.1 ml of the sample to be assayed or the reference antigen (0–500 pg). After incubation for 48 hours at 4° C., the free antigen is separated from the antigens bound to the antibodies by a precipitation with carbon-DEXTRAN T70 (0.5 ml per tube). The carbon-Dextran solution contains 5 g/l of neutral carbon, 500 mg of Dextran 70/l. After centrifugation (20 minutes, 3000 rpm, 4° C.), the radioactivity present in the supernatant is measured with a beta counter (Beckman) using liquid scintillation. The sensitivity of the assay is 20 pg/ml.

The accuracy of the method is 5%. The coefficients of the intra- and inter assay variation are 6% and 10% respectively. There is no cross reaction between this anti PGE2 antiserum and other prostanoids (Thromboxane B2, G-keto-PGF1-alpha, PGF2, PGA2), nor with the fatty acids such as arachidonic acid, oleic acid or also linoleic acid.

5. Analysis of the synthesis of DNA by measurement of the incorporation of $^3$H-thymidine After different culture durations, the chondrocytes are cultivated in nutritive medium with the addition of 2 uCi/ml (5 Ci/mmole) of methyl $^3$H-thymidine ($^3$H-TDN) (Amersham, Brussels, Belgium) for 24 hours. The chondrocyte clusters are then washed for 20 minutes using a phosphate-buffered saline (PBS-50 mM PO$_4$, 150 mM NaCl, pH 7.4) containing the same protease inhibitors as those used for the assay of the PGs. They are then incubated for 20 minutes in PBS containing unlabelled thymidine (100 µg/ml), then washed again twice for 20 minutes.

The cluster is then dissociated using ultrasonics (10 sec., 4° C., 200 watts/cm$^2$).

The radioactivity incorporated in the cluster is then measured using a beta scintillation counter.

6. DNA assay

The assay of the DNA content of the clusters is carried out on clusters dissociated using ultrasonics, according to the fluorimetric method described by Labarca and Paigen (1980).

The bisbenzimide fluorochrome reagent (BF) (Hoechst No. 3258—Calbiochem-Behring Cor.—La Jolla—Calif.) is added (4 g/tube) to a sample of clusters homogenized using ultrasonics. The fluorescence of the DNA-BF complexes is measured immediately with a fluorimeter (excitation wavelength: 256 nm, emission wavelength: 458 nm). Bovine DNA (0–5 µg) is used as a reference. The fluorescence of the complexes is directly proportional to the concentration of DNA.

7. Calculations and statistical analysis

The results are expressed in quantities of PG, coll. II or PGE2 measured in the culture medium (CM) per µg of DNA. The cumulative measurements are obtained by adding the quantities assayed in the CMs to each renewal of the CM, for successive periods: 0 to 4, 4 to 8, 8 to 12 days of culture. The total production of PG is calculated by adding the cumulative quantities measured in the CMs to those measured in the corresponding clusters. The mean and the standard deviation (m±s.d) are calculated. Comparison of the mean values is carried out using the Mann-Whitney U statistical test.

8. Production of OH° hydroxyl radicals

Principle of the method:

The products are dissolved in 10 ml flasks at the required concentration in phosphate buffer: $6.6.10^{-2}$M, pH 7.4 in the presence of alpha keto methiolbutyric acid ($10^{-3}$M: KMB). After the flasks have been hermetically sealed, the samples are irradiated with gamma rays provided by a $^{137}$Cs source.

The OH° radicals produced by the gamma radiation react with the KMB to produce the ethylene detected by a gas chromatograph. The height of the ethylene peak is proportional to the quantity of free radicals formed in the medium (Weis et al., 1978).

9. Antilipoperoxidizing activity

Principle of the method:

Similar to the preceding anti-radical method but where the KMB is replaced by linoleic acid (C18: 2), the gamma radiation releases pentane which is analyzed. The height of the pentane peak is proportional to the quantity free of radicals formed in the medium.

10. Production of the superoxide anion ($O^{°2}$) by the polymorphonuclear cells (PMNs).

Principle of the method:

This is measured with a double beam spectrophotometer which allows the reduction of ferricytochrome C by $O°_2$ to be monitored. The incubation medium (2.5 ml) is constituted by PBS buffer containing glucose (7.5 mM), ferricytochrome C (0.956 mM), CaCl$_2$ (2.3 mM), MgCl$_2$ (1.1 mM), $7.5.10^6$ of cells and the substance to be tested at a concentration of 0.032 mM. The reaction is triggered by adding phorbol myristate acetate at a final concentration of 0.012 mM and the reduction of the cytochrome C is monitored at 550 nm for 10 minutes. The reference cell contains the same material as that described above with an additional 48 µg of superoxide dismutase (SOD)/ml of medium.

II RESULTS RELATING TO THE PRODUCTS OF FORMULAE (Ia) (Ib) and (Ic):

Ia: GC-(4 alpha→8) EGC

Ib: GC-(4 alpha→8) GC

Ic: GC-(4 alpha→8) GC-(4 a→8)-GC

GC and EGC representing gallocatechin and epigallocatechin respectively with the following formulae:

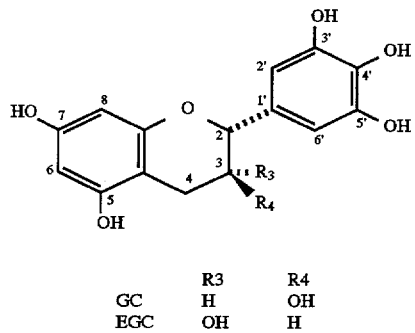

| | R3 | R4 |
|---|---|---|
| GC | H | OH |
| EGC | OH | H |

II-1 Incorporation of $^3$H thymidine in the chondrocytes, index of cell proliferation None of the substances Ia, Ib and Ic modifies the incorporation of $^3$H thymidine in the chondrocytes at the three doses tested 1, 10 and 100 pg/ml relative to control values.

11-2 Assay of the proteoglycans of type II collagen and prostaglandins E2

The experiments were carried out three times at intervals of several months under two different experimental conditions:

(1) in the absence of foetal calf serum but in a synthetic medium: 1% ULTROSER G (2) in the presence of 5% foetal calf serum.

A. IN THE PRESENCE OF ULTROSER

1. Proteoglycans (PG)

The amounts of PGs released in the culture medium and related to µg of DNA for each 4-day incubation period (µg/µg DNA/96 h) are set out in Tables 1, 2 and 3. Expressed in absolute and percentile cumulative amounts, it appears that the effects of the three substances are quite similar to each other (Table 4).

However, it should be noted that only substance Ic has a significant effect at a dose of 1 µg/ml (Table 3).

The concentrations of PG in the clusters are significantly stimulated and in a dose-dependent way by the three concentrations studied of substances Ia and Ic; for substance Ib, no significant effect is noted for the concentration of 1 µg/ml (Tables 5, 6, 7).

2. Type II collagen

The amounts of type II collagen released in the culture medium during a 4-day incubation period and expressed per µg of DNA (ng/µg DNA/96 h) are illustrated in Tables 8 (substance Ia), 9 (substance Ib) and 10 (substance Ic). Only substance Ic exerts a significant effect at the lowest dose experimented with: 1 µg/ml. The cumulative release over 12 days expressed in absolute values and in percentile values is set out in Table 11. They are practically identical for the three substances Ia, Ib and Ic.

The values for collagen II in the clusters over 12 days expressed in ng per µg of DNA in the clusters over 12 days are set out in Table 12. Substance Ic is the only one which is a stimulant at the dose of 1 µg/ml.

3. Prostaglandins E2 (PGE2)

The prostaglandins were assayed in culture media corresponding to the incubation of the 4th to 8th day, a period when the cluster is formed.

The three substances significantly reduce the amounts of PGE2 (Table 13).

B. IN THE PRESENCE OF F.C.S.

Two experiments (cultures 397 and 403) were carried out in order to confirm the results. They were simplified, on the one hand by carrying out the cultures for 8 days instead of 12 days, and on the other hand, only two doses of products Ia, Ib and Ic were studied: 10 and 100 µg/ml.

1. Proteoglycans (PG)

The PGs released in the culture medium and expressed in µg/ µg of DNA/96 h are significantly increased in the presence of 10 and 100 µg/ml. A dose-response effect was observed for the three substances (Tables 14 and 15).

The PGs in the clusters are also significantly increased during the incubation of substances Ia, Ib and Ic at concentrations of 10 and 100 µg/ml.

A dose-dependent effect is observed (Tables 16 and 17). These results are observed for the two experiments performed: cultures 397 and 403.

2. Type II collagen

The type II collagen increases in the culture media when the chondrocytes are incubated with substances Ia, Ib and Ic at concentrations of 10 and 100 µg/ml. The response is dose-dependent (Tables 18 and 19). In the clusters, an accident occurred which only allowed the collagen II to be assayed during experiment 397. An increase in collagen II is observed for the 3 substances Ia, Ib and Ic at concentrations of 10 and 100 µg/ml. The effect is dose-dependent (Table 20).

3. Prostaglandins E2 (PGE2) (Table 13)

A significant inhibiting effect is observed for the three substances at 10 and 100 µ/ml (except during the first incubation period day 0–4 for 10 µg/ml of substance Ia) for the two incubation periods from 0 to the 4th day and from the th to the 8th day (Table 21).

II-3. Production of the OH° hydroxyl radical Results:

The addition of substances Ia, Ib and Ic significantly inhibits the production of free radicals from KMB (Table 22) or from linoleic acid (Table 23). At doses of $10^{-5}M$ the substances tested still have an action on the KMB model. On the other hand, they have no effect on the model using linoleic acid as substrate.

II-4. Production of a superoxide anion ($O°_2$) by the polymorphonuclear cells (PMNs).

Results:

In the presence of substances Ia and Ib, the reduction of ferricytochrome C is strongly reduced therefore suggesting that the product acts either by trapping the superoxide anion, or by inhibiting the enzymatic system of the PMNs responsible for the production of this activated oxygenated type. However, control experiments indicate that product Ia as well as Ib, Ic and esculoside are by themselves powerful reducers of ferricytochrome C. This effect not being quantifiable, no conclusion can consequently be drawn on a possible inhibiting effect of these products on the production of the superoxide anion by the activated PMNs.

III—Conclusion of the study of proanthocyanidols on the model of human chondrocytes in tridimensional culture Substances Ia, Ib and Ic act on the model studied by:

1. significantly increasing the production of proteoglycans, assayed by the radio immunological method, in the culture medium and in the newly-formed cluster;

2. significantly increasing the production of type II collagen assayed by the radio immunological method, in the culture medium and in the newly-formed cluster;

3. significantly reducing the production of prostaglandins E2 in the culture media during the first two culture periods from the 1st to the 4th day, and from the 4th to the 8th day;

4. significantly reducing the ON° free radicals produced in the presence of either KMB, or linoleic acid.

The results were reproduced over three consecutive experiments under two conditions of medium culture: in the presence of 1% Ultroser and in the presence of foetal calf serum.

These substances have a profile of a chondroprotective medicament.

The tables indicated above are as follows:

TABLE 1

PGs RELEASED IN THE CULTURE MEDIUM
(µg/µg DNA/96 h)

| CULTURE TIME | SUBSTANCE Ia (µg/ml) | | | |
|---|---|---|---|---|
| (DAYS) | 0 | 1 | 10 | 100 |
| 0–4 | 13.6 ± 1.6 | 14.2 ± 1.6 | 22.4 ± 0.2* | 28.6 ± 2.85* |
| 4–8 | 1.96 ± 0.24 | 1.74 ± 0.18 | 3.26 ± 0.12* | 3.94 ± 0.1* |
| 8–12 | 0.42 ± 0.03 | 0.44 ± 0.04 | 0.74 ± 0.18* | 0.78 ± 0.02* |

*: $p < 0.025$ compared with the controls

TABLE 2

PGs RELEASED IN THE CULTURE MEDIUM
(µg/µg DNA/96 h)

| CULTURE TIME | SUBSTANCE Ib (µg/ml) | | | |
|---|---|---|---|---|
| (DAYS) | 0 | 1 | 10 | 100 |
| 0–4 | 13.7 ± 1.66 | 13.0 ± 1.22 | 20.4 ± 3.0* | 28.2 ± 2.92* |
| 4–8 | 3.14 ± 0.14 | 3.45 ± 0.56 | 4.78 ± 0.56* | 5.65 ± 0.24* |
| 8–12 | 0.71 ± 0.09 | 0.72 ± 0.08 | 1.00 ± 0.12* | 1.32 ± 0.01* |

*: $p < 0.025$ compared with the controls (Mann-Whitney U-test)

TABLE 3

PGs RELEASED IN THE CULTURE MEDIUM
(µg/µg DNA/96 h)

| CULTURE TIME | SUBSTANCE Ic (µg/ml) | | | |
|---|---|---|---|---|
| (DAYS) | 0 | 1 | 10 | 100 |
| 0–4 | 12.4 ± 0.96 | 15.9 ± 1.15* | 19.1 ± 1.2* | 21.1 ± 1.0* |
| 4–8 | 3.0 ± 0.15 | 3.7 ± 0.15* | 4.4 ± 0.52* | 4.9 ± 0.45* |
| 8–12 | 1.04 ± 0.07 | 1.32 ± 0.7* | 1.53 ± 0.15* | 1.75 ± 0.05* |

*: $p < 0.025$ (Mann-Whitney U-test)

TABLE 4

| | Concentrations studied (µg/ml) | | | | | | | |
|---|---|---|---|---|---|---|---|---|
| | 0 | | 1 | | 10 | | 100 | |
| | Proteoglycans released during the 12 days of culture | | | | | | | |
| Substances | µg/ µg DNA/ 12 days | | µg/ µg DNA/ 12 days | | µg/ µg DNA/ 12 days | | µg/ µg DNA/ 12 days | |
| No. | Abs | % | Abs | % | Abs | % | Abs | % |
| Ia | 16 | 100 | 16.4 | 103 | 26.4 | 165 | 33.3 | 208 |
| Ib | 17.6 | 100 | 17.2 | 98 | 26.3 | 149 | 35.2 | 200 |
| Ic | 16.4 | 100 | 20.9 | 127 | 25 | 150 | 27.8 | 170 |

TABLE 5

PG IN THE CLUSTERS over 12 days (ng/µg DNA)

| AGE OF THE CULTURE | SUBSTANCE Ia (µg/ml) | | | |
|---|---|---|---|---|
| (DAYS) | 0 | 1 | 10 | 100 |
| 0–12 | 581 ± 98 | 912 ± 83.6* | 1411 ± 153* | 2105 ± 42* |

*: $p < 0.025$ compared with the controls (Mann-Whitney U-test)

TABLE 6

PG IN THE CLUSTERS over 12 days (ng/µg DNA)

| AGE OF THE CULTURE | SUBSTANCE Ib (µg/ml) | | | |
|---|---|---|---|---|
| (DAYS) | 0 | 1 | 10 | 100 |
| 0–12 | 724 ± 222 | 742 ± 62* | 931 ± 24* | 1108 ± 45* |

*: $p < 0.025$ (Mann-Whitney U-test)

TABLE 7

PG IN THE CLUSTERS over 12 days (ng/µg DNA)

| AGE OF THE CULTURE | SUBSTANCE Ic (µg/ml) | | | |
|---|---|---|---|---|
| (DAYS) | 0 | 1 | 10 | 100 |
| 0–12 | 742 ± 50 | 886 ± 114* | 1046 ± 74* | 1184 ± 33* |

*: $p < 0.025$ (Mann-Whitney U-test)

TABLE 8

COLL. II RELEASED IN THE CULTURE MEDIUM (ng/µg DNA/96 h)

| CULTURE TIME | SUBSTANCE Ia (µg/ml) | | | |
|---|---|---|---|---|
| (DAYS) | 0 | 1 | 10 | 100 |
| 0–4 | 225 ± 22 | 233 ± 25 | 301 ± 52* | 462 ± 51* |
| 4–8 | 152 ± 14 | 147 ± 19 | 259 ± 22* | 311 ± 41* |
| 8–12 | 97.4 ± 18 | 102.2 ± 10.96 | 147 ± 21* | 109 ± 23* |

*: $p < 0.025$ (Mann-Whitney U-test)

TABLE 9

COLL. II RELEASED IN THE CULTURE MEDIUM (ng/µg DNA/96 h)

| CULTURE TIME | SUBSTANCE Ib (µg/ml) | | | |
|---|---|---|---|---|
| (DAYS) | 0 | 1 | 10 | 100 |
| 0–4 | 204 ± 21 | 222 ± 26 | 322 ± 33* | 392 ± 46* |
| 4–8 | 102 ± 12 | 112 ± 19 | 158 ± 14* | 190 ± 22* |
| 8–12 | 62.8 ± 6.9 | 59.9 ± 0.6 | 91.7 ± 6.1* | 137.7 ± 13.4* |

*: $p < 0.025$ (Mann-Whitney U-test)

TABLE 10

COLL. II RELEASED IN THE CULTURE MEDIUM (ng/µg DNA/96 h)

| CULTURE TIME | SUBSTANCE Ic (µg/ml) | | | |
|---|---|---|---|---|
| (DAYS) | 0 | 1 | 10 | 100 |
| 0–4 | 107.8 ± 0.3 | 149.4 ± 8.7* | 162 ± 11* | 182 ± 5.6* |
| 0–8 | 52.2 ± 5.4 | 65.8 ± 7.4* | 70.5 ± 7.1* | 93.8 ± 10.5* |
| 0–12 | 32.2 ± 3.4 | 41.2 ± 4.6* | 50.6 ± 4.2* | 61.1 ± 5.2* |

*: $p < 0.025$ (Mann-Whitney U-test)

TABLE 11

| | Doses studied (µg/ml) | | | | | | | |
|---|---|---|---|---|---|---|---|---|
| | 0 | | 1 | | 10 | | 100 | |
| | Cumulative release of coll.II over 12 days | | | | | | | |
| Substances | µg/ µg DNA/ 12 days | | µg/ µg DNA/ 12 days | | µg/ µg DNA/ 12 days | | µg/ µg DNA/ 12 days | |
| No. | Abs | % | Abs | % | Abs | % | Abs | % |
| Ia | 474 | 100 | 482 | 102 | 787 | 166 | 962 | 202 |
| Ib | 369 | 100 | 394 | 107 | 572 | 155 | 728 | 197 |
| Ic | 191 | 100 | 256 | 134 | 292 | 153 | 337 | 176 |

Absolute value: expressed in ng/µg DNA/12 days

TABLE 12

Average concentrations (m ± SD) of type II collagen in the clusters of chondrocytes at the end of 12 days of culture

| | Doses studied | | | |
|---|---|---|---|---|
| Subs. No. | 0 | 1 µg/ml | 10 µg/ml | 100 µg/ml |
| Ia | 104 ± 15.1 | 105 ± 13 | 165 ± 21** | 175 ± 19** |
| Ib | 90 ± 10 | 98 ± 9 | 121 ± 10** | 158 ± 16** |
| Ic | 61 ± 7 | 81 ± 6* | 94 ± 7** | 121 ± 13** |

*: $p < 0.05$
**: $p < 0.01$

TABLE 13

Amounts of PGE2 (pg/μg of DNA) in the culture media taken on the 4th and 8th day

| Subs. No. | Doses studied | | | |
|---|---|---|---|---|
| | 0 | 1 μg/ml | 10 μg/ml | 100 μg/ml |
| Ia | 122 ± 39 | 91.5 ± 9 | 44 ± 0.6* | 25 ± 13** |
| Ib | 146 ± 23 | 129 ± 19 | 76 ± 14** | 48 ± 15** |
| Ic | 138 ± 19 | 101 ± 7* | 81 ± 12** | 39 ± 10** |

*: $p < 0.025$
**: $p < 0.01$

TABLE 14

PG IN THE CULTURE MEDIUM (μg/μg DNA - 96 H)

| CULTURE TIME | | Substance Ia | | Substance Ib | | Substance Ic | |
|---|---|---|---|---|---|---|---|
| (DAYS) | 0 | 10 | 100 | 10 | 100 | 10 | 100 |
| 0–4 | 6.5 ± 0.75 (100%) | 7.7 ± 0.49* (118.5%) | 9.5 ± 1.34* (147%) | 7.6 ± 0.41* (117%) | 11.9 ± 2.09* (183.5%) | 7.8 ± 1.51* (120%) | 10.4 ± 1.19* (160%) |
| 4–8 | 1.99 ± 0.19 (100%) | 2.37 ± 0.17* (119%) | 2.69 ± 0.15* (135%) | 2.32 ± 0.21* (117%) | 2.71 ± 0.24* (136%) | 2.34 ± 0.08* (118%) | 2.40 ± 0.35* (121%) |

*$p < 0.025$ compared with the non-treated controls (Mann-Whitney U-test)

TABLE 15

PG IN THE CULTURE MEDIUM (μg/μg DNA - 96 H)
SUBSTANCE (μg/ml)

| CULTURE TIME | | Ia | | Ib | | Ic | |
|---|---|---|---|---|---|---|---|
| (DAYS) | 0 | 10 | 100 | 10 | 100 | 10 | 100 |
| 0–4 | 5.3 ± 0.38 (100%) | 6.9 ± 0.99* (131%) | 8.8 ± 1.49* (166%) | 7.1 ± 0.36* (134%) | 7.9 ± 0.30* (149%) | 7.0 ± 1.19* (132%) | 7.5 ± 0.96* (140%) |
| 4–8 | 1.7 ± 019 (100%) | 2.1 ± 0.21* (123%) | 2.4 ± 0.09* (138%) | 2.1 ± 1.16* (125%) | 2.3 ± 0.13* (137%) | 2.0 ± 0.17* (117%) | 2.4 ± 0.25* (138%) |

*$p < 0.025$ (Mann-Whitney U-test)

TABLE 16

PG IN THE CLUSTERS OVER 8 DAYS (ng/μg DNA)

| CULTURE TIME | | Substance Ia | | Substance Ib | | Substance Ic | |
|---|---|---|---|---|---|---|---|
| (DAYS) | 0 | 10 | 100 | 10 | 100 | 10 | 100 |
| 0–8 | 784 ± 105 (100%) | 1004 ± 56* (128%) | 1242 ± 208* (158%) | 1108 ± 166* (141%) | 1142 ± 110* (146%) | 915 ± 75* (117%) | 1035 ± 121* (132%) |

*: $p < 0.025$ compared with the non-treated controls (Mann-Whitney U-test)

TABLE 17

PG IN THE CLUSTERS (ng/µg DNA)
over 8 days

| CULTURE TIME | | Substance Ia (µg/ml) | | Substance Ib (µg/ml) | | Substance Ic (µg/ml) | |
|---|---|---|---|---|---|---|---|
| (DAYS) | 0 | 10 | 100 | 10 | 100 | 10 | 100 |
| 0–8 | 576.0 ± 40.55 (100%) | 688.8 ± 40.65* (120%) | 829.4 ± 9.37* (144%) | 724.0 ± 72.45* (126%) | 832.0 ± 59.10* (144%) | 718.2 ± 62.61* (125%) | 799.5 ± 85.9* (139%) |

*: $p < 0.025$ compared with the non-treated controls

TABLE 18

COLL. II RELEASED IN THE CULTURE MEDIUM
(ng/µg DNA/96 H)

| CULTURE TIME | | Substance Ia (µg/ml) | | Substance Ib (µg/ml) | | Substance Ic (µg/ml) | |
|---|---|---|---|---|---|---|---|
| (DAYS) | 0 | 10 | 100 | 10 | 100 | 10 | 100 |
| 0–4 | 32.7 ± 5.59 | 44.3 ± 2.30* | 77.0 ± 15.58* | 41.4 ± 0.51* | 81.1 ± 20.2* | 44.1 ± 6.98* | 70.7 ± 10.3* |
| 4–8 | 25.9 ± 5.10 | 34.0 ± 3.11* | 47.2 ± 5.19* | 33.3 ± 4.61* | 55.0 ± 17.21* | 33.5 ± 3.71* | 41.7 ± 3.69* |

*: $p < 0.025$ compared with the non-treated controls (Mann-Whitney U-test)

TABLE 19

COLL. II RELEASED IN THE CULTURE MEDIUM
(ng/µg DNA/96 H)

| CULTURE TIME | | Substance Ia (µg/ml) | | Substance Ib (µg/ml) | | Substance Ic (µg/ml) | |
|---|---|---|---|---|---|---|---|
| (DAYS) | 0 | 10 | 100 | 10 | 100 | 10 | 100 |
| 0–4 | 23.0 ± 3.91 | 37.4 ± 1.98* | 44.2 ± 11.6* | 38.2 ± 2.60* | 56.3 ± 12.41* | 37.9 ± 5.47* | 53.2 ± 4.21* |
| 4–8 | 16.3 ± 1.72 | 25.3 ± 2.20* | 38.2 ± 5.71* | 29.6 ± 3.44* | 46.3 ± 2.61* | 23.3 ± 2.11* | 33.5 ± 1.73* |

*: $p < 0.025$ (Mann-Whitney U-test)

TABLE 20

COLL. II IN THE CLUSTERS (ng/µg DNA)

| CULTURE TIME | | Substance Ia (µg/ml) | | Substance Ib (µg/ml) | | Substance Ic (µg/ml) | |
|---|---|---|---|---|---|---|---|
| (DAYS) | 0 | 10 | 100 | 10 | 100 | 10 | 100 |
| 4–8 | 62.8 ± 4.90 | 78.8 ± 10.5* | 114.7 ± 10.55* | 81.6 ± 16.00* | 113.2 ± 18.25* | 85.9 ± 14.45* | 109.8 ± 8.52* |

*: $p < 0.025$ (Mann-Whitney U-test)

TABLE 21

| | PGE2 IN THE CULTURE MEDIUM (pg/μg DNA/96 H) | | | | | | |
|---|---|---|---|---|---|---|---|
| CULTURE TIME | | Substance Ia (μg/ml) | | Substance Ib (μg/ml) | | Substance Ic (μg/ml) | |
| (DAYS) | 0 | 10 | 100 | 10 | 100 | 10 | 100 |
| 0–4 | 300 ± 17 | 312 ± 15 | 143 ± 25* | 130 ± 21* | 121 ± 16* | 160 ± 17* | 153 ± 15* |
| 4–8 | 48 ± 3.5 | 27 ± 2.5* | 25 ± 3.5* | 30 ± 1.7* | 25 ± 1* | 35.5 ± 2.1* | 29 ± 3.5* |

*: $p < 0.025$ compared with the non-treated controls (Mann-Whitney U-test)

TABLE 22

Inhibition (expressed in % relative to the controls) of the production of hydroxyl radicals by substances Ia, Ib and Ic.
Substrate: KMB

| Products | % INHIBITION | | |
|---|---|---|---|
| | Ia | Ib | Ic |
| concentration | | | |
| $10^{-3}$M | 78 | 80 | 74 |
| $10^{-4}$M | 41 | 46 | 39 |
| $10^{-5}$M | 22 | 25 | 20 |

TABLE 23

Inhibition (expressed in % relative to the controls) of the production of hydroxyl radicals by substances Ia, Ib and Ic.
Substrate: Linoleic acid

| Products | % INHIBITION | | |
|---|---|---|---|
| | Ia | Ib | Ic |
| concentration | | | |
| $10^{-3}$M | 94 | 93 | 91 |
| $10^{-4}$M | 42 | 45 | 40 |
| $10^{-5}$M | 0 | 0 | 0 |

REFERENCES

Bassleer C., Gysen P., Foidart J. M., Bassleer R., Franchimont P.: Human chondrocytes in tridimensional culture. In vitro, 1986, 22: 113–119

Bayliss M. T., Venn M.: Chemistry of human articular cartilage. In: Maroudas A., Holborow E. J., eds. Studies in joint diseases, 1st ed. London: Pitman Medical, 1980, 2–58

Franchimont P., Bouffioux Ch., Reuter A. et al. Radioimmunoassay of prostatic acid phosphatase: validation and clinical application. Int. J. Cancer. 1983, 89: 114–124

Franchimont P., Bassleer C., Henrotin Y., Gysen P., Bassleer R.: Effects of human and salmon calcitonin in human articular chondrocytes cultivated in clusters. J. Clin. Endocr. Metab., 1989, 69:259–266

Franchimont P., Bassleer C.: New diagnostic tools and methodological approaches; an outlook to the future. Scand. J. of Rheumatol., 1989, 80: 29–31

Franchimont P., Bassleer C.: Effects of hormones and local growth factors on articular chondrocyte metabolism. Scand. J. of Rheumatol., 1991, suppl. 27, 18: 68: 70

Greenwood F.C., Hunter W., Glover J.: The preparation of $^{131}$I-labelled human growth hormone of high specific radioactivity. Biochem. J. 1973, 89: 114–24

Gysen P., Franchimont P.: Radioimmunoassay of proteoglycans J. Immunoassay., 1984, 5: 221–243

Henrotin Y., Bassleer C., Collette J., Nusgens B., Franchimont P.: Radioimmunoassay for human type II collagen. J. of Immunoassay, 1990, 11(4): 555–578

Herbage D., Bouillet J., Bernengo J. C.: Biochemical and physico-chemical characterization of pepsin-solubilized type II collagen from bovine articular cartilage. Biochem. J. 1977, 161: 303–312

Labarca C., Paigen K.: A simple, rapid and sensitive DNA assay procedure. Anal. Blochem., 1980, 102: 344–352

Oegema T. R., Hascall V. C., Dziewatkowski D. D.: Isolation and characterization of proteoglycans from the swarm rat chondrosarcoma. J. Biol. Chem. 1975, 250: 6151–6159

Roughley P .J., Mc Nicol D., Santer V., Buckwalter J. The presence of a cartilage-like proteoglycan in the adult human meniscus. Biochem. J. 1981, 197: 77–83

Salacynsky p., Hope J., Mc Lean C. et al.: A new simple method which allows theoretical incorporation of radio-iodine into proteins and peptides without damage. J. Endocrinol. 1979, 81: 131

Serteyn D., Deby-Dupont G., Pincemail J., Mottart E., Philippart C., Lamy M.: Equine post-anaesthesic myositis: thromboxane, prostacyclin and prostaglandin E2 production. Vet. Res. Com., 1988, 12: 219–226

Vaitukaitis J., Robbins J. B., Nieschlag E., Ross G. T.: A method for producing specific antisera with small doses of immunogen. J. Clin. Endocrinol. Metab. 1971, 33: 988–91

Weiss S. S., Rustagi P. K., Lobuglio A. F.: Human generation of hydroxyl radical. J. Exp. Med., 1978, 147: 316–324

What is claimed is:

1. Method for treating articular pathologies assosciated with destruction of the cartilige, comprising administering to a patient in need of such treatment a medicament containing an effective amount of at least one prodelphinidin of the formula

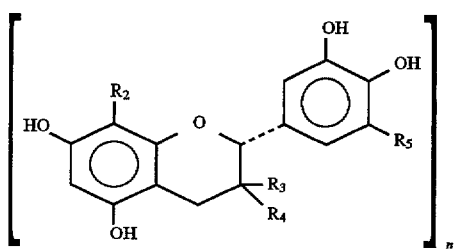

in which:

$R_1$ and $R_2$ independently repesent H or OH, $R_3$ and $R_4$ are defferent and represent H or OH, pl $R_5$ represents H or OH, and, n is an integer from 2 to 40, wherein at least one of the 2 to 40 units described above has $R_3$=H and $R_4$=OH, or $R_3$=OH and $R_4$=H, and $R_5$ represents OH.

2. Method according to claim 1, wherein the prodelphinidins are of the following formula:

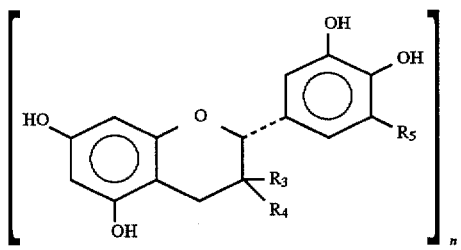

in which $R_3$, $R_4$ and $R_5$ are as defined in claim 1.

3. Method according to claim 1, wherein the medicament is prepared for administration by oral, parenteral or topical route.

4. Method according to claim 1, wherein the prodelphinidins are those originating from the Ribes species.

5. Method according to claim 4, wherein the prodelphinidins are contained in extracts of *Ribes nigrum*.

6. Method according to claim 5, wherein the prodelphinidins are isolated and purified from extracts of *Ribes nigrum*.

7. Method according to claim 1, wherein the prodelphinidins contain at least one of the following molecules:

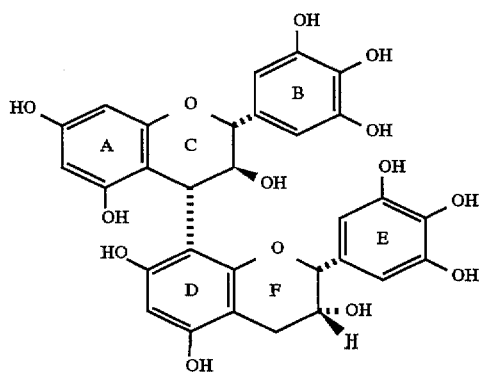

-continued

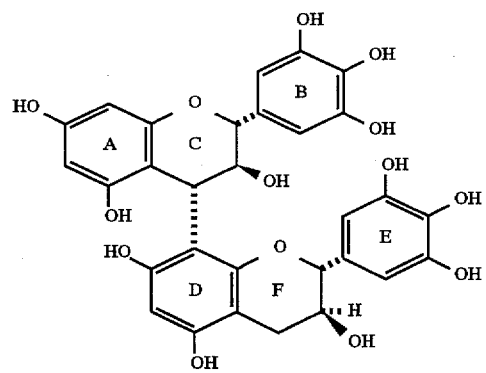

or

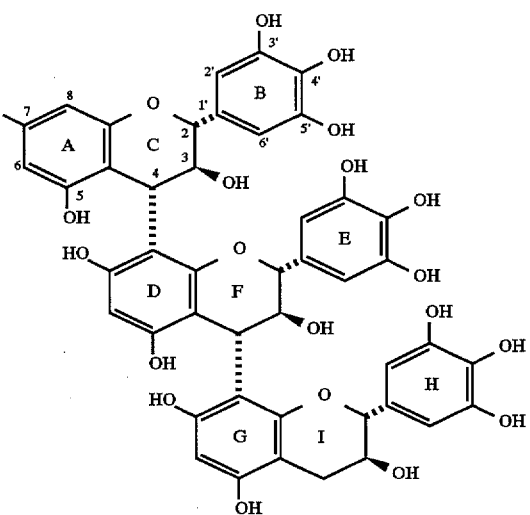

* * * * *